United States Patent
Hughes et al.

(10) Patent No.: US 11,255,711 B1
(45) Date of Patent: Feb. 22, 2022

(54) REAL TIME ADDITIVE PROCESSING SYSTEM FOR CRUDE OIL, FUELS, OR REFINED PRODUCTS AND METHOD

(71) Applicant: Cajun Technology Solutions, LLC, Baton Rouge, LA (US)

(72) Inventors: Brett Hughes, Baton Rouge, LA (US); Stuart Folse, Missouri City, TX (US)

(73) Assignee: Cajun Technology Solutions, LLC, Baton Rouge, LA (US)

( * ) Notice: Subject to any disclaimer, the term of this patent is extended or adjusted under 35 U.S.C. 154(b) by 0 days.

(21) Appl. No.: 17/224,706

(22) Filed: Apr. 7, 2021

(51) Int. Cl.
  *B67D 7/04* (2010.01)
  *G01F 9/00* (2006.01)
  *G01N 33/00* (2006.01)
  *B67D 7/16* (2010.01)

(52) U.S. Cl.
  CPC .............. *G01F 9/001* (2013.01); *B67D 7/04* (2013.01); *B67D 7/16* (2013.01); *G01N 33/0044* (2013.01)

(58) Field of Classification Search
  CPC ...... G01N 9/001; G01N 33/0044; B67D 7/16; B67D 7/04; B67D 7/32; B67D 7/743; B67D 7/78; B67D 7/68; B67D 7/744
  See application file for complete search history.

(56) References Cited

U.S. PATENT DOCUMENTS

| 2018/0237289 A1* | 8/2018 | Markwardt | B67D 7/36 |
| 2020/0353901 A1* | 11/2020 | Nair | B60S 5/02 |
| 2020/0407210 A1* | 12/2020 | Reid | B67D 7/744 |

\* cited by examiner

*Primary Examiner* — Jason K Niesz
(74) *Attorney, Agent, or Firm* — Baker Donelson; Dorian B. Kennedy

(57) ABSTRACT

A real time additive processing system for crude oil or refined fuel products is coupled to a fuel transport line that transfers fuel from one storage tank to another storage tank. The fuel additive processing system includes a fuel additive storage tank coupled to a liquid conduit having a liquid pump with a speed/stroke controller that regulates the liquid pump. The liquid conduit is coupled to the fuel transport line at a fuel additive injection nozzle. The fuel additive processing system also includes a flow rate transmitter and a chemical or physical property analyzer coupled to the fuel transport line downstream of the additive injection nozzle. The flow rate transmitter transmits the flow rate of the fuel passing through the fuel transport line. The fuel additive processing system includes a flow controller that communicates with the liquid pump speed/stroke controller, flow rate transmitter and chemical or physical property analyzer.

18 Claims, 1 Drawing Sheet

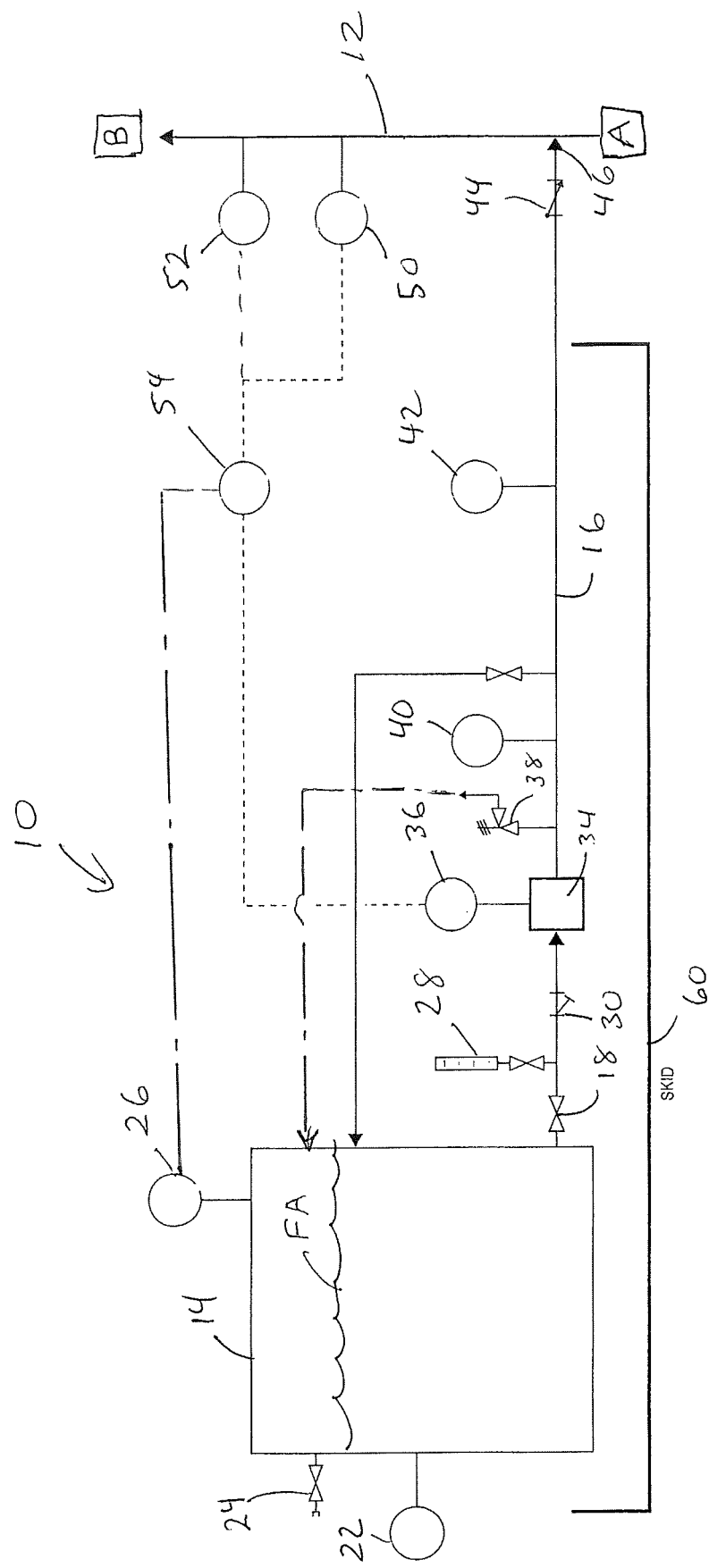

REAL TIME ADDITIVE PROCESSING SYSTEM FOR CRUDE OIL, FUELS, OR REFINED PRODUCTS AND METHOD

CROSS REFERENCE TO RELATED APPLICATIONS

Not applicable.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

TECHNICAL FIELD

This invention relates to a system for treating vast volumes of oil or fuel with select chemicals, and a method of utilizing such.

BACKGROUND OF THE INVENTION

This section is intended to introduce various aspects of the art, which may be associated with exemplary embodiments of the present disclosure. This discussion is believed to assist in providing a framework to facilitate a better understanding of particular aspects of the present disclosure. Accordingly, it should be understood that this section should be read in this light, and not necessarily as admissions of prior art.

Fuels and other oil products or refined products oftentimes include harmful chemicals or a physical attribute that should be controlled. Therefore, these products are treated with chemical additives to change the chemical or physical characteristics of the product. For example, hydrogen sulfide ($H_2S$) naturally occurs in crude oil. $H_2S$ also has detrimental effects on production equipment, as it is highly corrosive and can degrade process and storage infrastructure, leading to costly repairs. There are many safety hazards associated with $H_2S$. Therefore, it is important to effectively control the hydrogen sulfide within any volume of crude oil.

To control the $H_2S$ within large quantities of oil, an additive chemical or chemical additive may be added to the crude oil to scavenge the $H_2S$ and render it harmless. This is typically done subsequent to the transfer of oil from one storage area to another storage area, such as from storage tank to vessel, vessel to storage tank, or storage tank to storage tank, as the transfer creates a volumetric mixing or agitation of the crude oil, which helps in the distribution of the additive chemical throughout the volume of the crude oil. The chemical additive, such as monoethanoloamine (MEA) and monomethylamine (MMA) triazine is simply mixed with the large quantities of crude oil after the crude oil has been transfer from one oil receiving storage area to another. This is a batch type treatment of the crude oil volume. However, because of the dangers related to the $H_2S$, the amount of chemical additive added to the volume of crude oil is vastly greater than necessary to scavenge the $H_2S$ from the crude oil. This ensures that all the $H_2S$ is processed or scavenged from the crude oil. Typically, the overage amount of chemical additive is approximately 40%, i.e., 40% more scavenging chemical additive is added to the oil to ensures that all the $H_2S$ is processed. This vast overage of a chemical additive is inefficient and creates an unnecessarily high expense in processing the oil.

Accordingly, a need exists for a system and method of processing a refined products, fuels, or oil in a more efficient manner. It is to the provision of such therefore that the present invention is primarily directed.

BRIEF SUMMARY OF THE INVENTION

A real-time fuel additive processing system for use in conjunction with a fuel transport line transporting a fuel containing a target chemical to be treated, the fuel additive processing system comprises a fuel additive storage tank, a fuel additive injection nozzle in fluid communication with the fuel transport line, a fuel additive liquid conduit extending from the fuel additive storage tank to the fuel additive injection nozzle, a liquid pump coupled to the fuel additive liquid conduit, a flow rate transmitter for sensing the flow rate of fuel through the fuel transport line and transmitting the sensed flow rate, a chemical analyzer coupled to the fuel transport line for sensing the quantity of a target chemical within the fuel flowing through the fuel transport line, and a flow rate controller electronically coupled to the flow rate transmitter, the chemical analyzer, and the liquid pump. The flow rate transmitter sending an electronic signal to the flow rate controller indicating the flow rate of liquid through the fuel transport line. The chemical analyzer sending an electronic signal to the flow rate controller indicating the quantity of a sensed target chemical within the fuel flowing through the fuel transport line. The flow rate controller controlling the operation of the liquid pump to control the amount of fuel additive passing through the nozzle and into the fuel flowing through the fuel transport line for the treatment of the target chemical within the fuel.

A method of processing flowing fuel passing through a fuel transport line comprises the steps of (A) providing a fuel additive storage tank containing a volume of fuel additive, a fuel additive injection nozzle in fluid communication with the fuel transport line, a fuel additive liquid conduit extending from the fuel additive storage tank to the fuel additive injection nozzle, a liquid pump coupled to the fuel additive liquid conduit, a flow rate transmitter for sensing the flow rate of fuel through the fuel transport line and transmitting the sensed flow rate, a chemical analyzer coupled to the fuel transport line for sensing the quantity of a target chemical within the fuel flowing through the fuel transport line, and a flow rate controller electronically coupled to the flow rate transmitter, the chemical analyzer, and the liquid pump; (B) sensing the flow rate of the fuel passing through the fuel transport line and sending a signal of the sensed flow rate from the flow rate transmitter to the flow rate controller; (C) sensing the quantity of target chemical within the fuel passing through the fuel transport line through the chemical analyzer and sending an electronic signal of the sensed quantity of target chemical to the flow rate controller; (D) determining a quantity of fuel additive to be added to the fuel flowing through the fuel transport line by the flow rate controller, and (E) sending an electronic signal from the flow rate controller to the liquid pump to control the operation of the liquid pump to regulate the amount of fuel additive passing through the nozzle and into the fuel flowing through the fuel transport line for the treatment of the target chemical within the fuel.

BRIEF DESCRIPTION OF THE DRAWINGS

So that the manner in which the present inventions can be better understood, certain illustrations, charts and/or flow charts are appended hereto. It is to be noted, however, that the drawings illustrate only selected embodiments of the inventions and are therefore not to be considered limiting of scope, for the inventions may admit to other equally effective embodiments and applications.

FIG. 1 is a schematic view of a fuel additive processing system embodying principles of the invention in a preferred form.

DETAILED DESCRIPTION OF CERTAIN EMBODIMENTS

Definitions

For purposes of the present disclosure, it is noted that spatially relative terms, such as "up," "down," "right," "left," "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over or rotated, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

DESCRIPTION OF SELECTED SPECIFIC EMBODIMENTS

With reference next to the drawings, there is a shown a real time fuel additive processing system for continuously treating flowing crude oil, refined fuel products, or fuel products, reference hereinafter simply as a fuel additive processing system 10, embodying principles of the invention in a preferred form. The fuel additive processing system 10 may be used for the treatment of crude oil, diesel oil, gasoline, refined products, fuel, or other fuel products, which are referenced herein collectively as "fuel". The fuel additive processing system 10 is coupled to a conventional fuel transport line 12 that transfers large quantities of liquid fuel from one storage vessel or tank A to another storage vessel or tank B. These fuel transport lines 12 typically transfer 12,000 to 15,000 barrels of liquid per hour and have an internal pressure of 30 to 50 p.s.i. The storage tanks A and B may be land based storage tanks, liquid tanker trucks, liquid tanker ships, or any other large liquid container.

The fuel additive processing system 10 includes a fuel additive storage tank 14 in fluid communication with a liquid conduit or line 16 through an/off valve 18. The storage tank 14 can contain a large volume of a liquid fuel additive FA, such as 10,000 gallons. The storage tank 14 has a temperature sensor/transmitter 22, a fill line outlet valve 24, and an additive level transmitter 26. The additive level transmitter 26 may be a EchoTouch US06 made by Flowline of Los Alamitos, Calif. The temperature sensor/transmitter 22 measures the temperature of the liquid contained within the storage tank 14. A manual flow indicator 28, in the form of a calibration column, is coupled to the liquid conduit 16 to measure the flow rate through the liquid conduit 16. A drain valve 30 is also coupled to the liquid conduit 16.

An additive liquid pump 34 is coupled to the liquid conduit 16 to flow the fuel through the liquid conduit 16. The liquid pump 34 may be a Neptune 535-S-N3-FA-100737-T-EC500, which has a capacity of 18 GPH, a DP/DT of 100 PSI (250 PSI max) with a ⅓ HP motor at 1,750 RPM made by Neptune Chemical Pump Co., Inc. of Lansdale, Pa. The liquid pump 34 is actuated through a speed/stroke controller 36 that is regulated through the electric current passing to the speed/stroke controller 36. The speed/stroke controller 36 may be a model number Neptune EC5000 made by Neptune Chemical Pump Co., Inc. of Lansdale, Pa. The liquid pump 34 and speed/stroke controller 36 are shown as separate items, however, the liquid pump 34 may include a speed/stroke controller 36 as a single unit. A pressure safety valve 38 is also coupled to the liquid conduit 16 so that a portion of the liquid passing through the liquid conduit 16 may pass back to the storage tank 14 should a threshold liquid high pressure be reached. A pressure gauge or indicator 40 is coupled to the liquid conduit 16 to indicate internal fluid pressure. The pressure gauge 40 may be a model number PN7692 made by IFM Efector, Inc. of Malvern, Pa. A flow transmitter 42 that determines the flow rate of the fuel additive through the liquid conduit 16 is coupled to the liquid conduit 16. The flow transmitter 42 may be a model number JVS-12KG/RT-30 made by AW Lake of Oak Creek, Wis. A check valve 44 is coupled to the liquid conduit 16 adjacent to an end of the liquid conduit 16 having a fuel additive injection nozzle 46 at a junction of the liquid conduit 16 and the fuel transport line 12.

The fuel additive processing system 10 also includes a flow rate transmitter 50 and a chemical or physical property analyzer 52 coupled to the fuel transport line 12 downstream of the additive injection nozzle 46. The flow rate transmitter 50 transmits the liquid flow rate of the fuel passing through the fuel transport line 12. The flow rate transmitter may be a model Fluxus F808 made by Flexim GmbH of Berlin, Germany. Lastly, the fuel additive processing system 10 includes a flow controller 54 that communicates with the liquid pump speed/stroke controller 36, flow rate transmitter 50 and chemical or physical property analyzer 52. The flow controller 54 includes a processor, software, and memory. The flow controller 54 may be a model number CompactLogix 1769-L30ERM sold by Allen-Bradley of Rockwell Automation, Inc. All electronic communications to the flow controller 54 may be done wirelessly or through hard wires.

The fuel additive processing system 10 may be mounted on a skid 60, or other movably platform, to enable the fuel additive processing system 10 to be moved from one location to another location.

In use, the fuel additive storage tank 14 is filled or partially filled with a chemical fuel additive FA to be added to a select flowing fuel or oil supply through the fuel transport line 12 for the treatment thereof. For example, for the treatment of crude oil, the fuel additive may be monoethanoloamine (MEA) and/or monomethylamine (MMA) triazine that is utilized to scavenge the dangerous target chemical of hydrogen sulfide H2S from the crude oil. However, the present system may be used for any refined product, fuel or oil and is not limited to the examples provided herein. The fuel additive may also be a lubricity additive such as SR2009 made by Dorf Ketal Chemicals LLC of Houston, Tex., an antistatic agent or conductivity improver such as SR1795 made by Dorf Ketal Chemicals LLC of Houston, Tex., a cold flow improver such as SR1690 made by Dorf Ketal Chemicals LLC of Houston, Tex., or other chemical additive intended to refine, treat or otherwise process a fuel or oil product.

With the commencement of the flow of a fuel product through the fuel transport line 12, the fuel additive processing system 10 commences its operation. As the fuel flows through the fuel transport line 12 the flow transmitter 50 continually senses the flow and determines the fuel's flow rate. The chemical or physical property analyzer 52 continually monitors the level of a target chemical or physical property within the fuel transport line 12. An example of a physical property that may be monitored is the conductivity of diesel oil, wherein the diesel oil is treated to have a conductivity within a select range. An example of a monitored chemical may be hydrogen sulfide (H2S) within crude oil within the fuel transport line 12. As such, with the transportation of crude oil through the fuel transport line 12, the chemical or physical property analyzer 52 is an analyzer which senses the level a hydrogen sulfide ($H_2S$) for treatment or scavenging by an additive chemical (fuel additive FA), such as monoethanoloamine (MEA) and monomethylamine (MMA) triazine. For this example, the chemical or physical property analyzer 52 may be a model number OMA-300 made by Applied Analytics, Inc or Burlington, Mass. The flow rate sensed or determined by the flow transmitter 50 and target chemical (H2S) level sensed or determined by the chemical or physical property analyzer 52 is electronically sent to the flow controller 54. The flow controller 54 then continuously determines the amount of fuel additive FA to inject into the fuel flowing through the fuel transport line 12.

Should the flow controller 54 determine that the level of a target chemical is above an acceptable level or acceptable range of level (too high), and therefore the amount of the full additive FA treatment chemical injected into the fuel is inadequate, the flow controller 54 immediately increases the flow rate of the treating fuel additive FA treatment chemical entering the fuel transport line 12 through nozzle 46 to compensate for the sensed elevated level of target chemical. The increase in the amount of treatment fuel additive FA is accomplished by the flow controller 54 sending a signal to the speed/stroke controller 36, which in turn controls an increase in the speed or stroke of the liquid pump 34 to increase the flow rate of the fuel additive FA being injected into the fuel within the fuel transport line 12. The increase in speed/stroke of the liquid pump 34 causes more, or a greater rate of, fuel additive FA treatment chemical to flow from the fuel additive storage tank 14, through liquid conduit 16, and through additive injection nozzle 46 into the fuel flowing through the fuel transport line 12.

Should the flow controller 54 determine that the level of a target chemical is below an acceptable level or acceptable range of levels (too low), and therefore the amount of the full additive FA treatment chemical injected into the fuel is too much and wasteful, the flow controller 54 immediately decreases the flow rate of the treating fuel additive FA treatment chemical entering the fuel transport line 12 through nozzle 46 to compensate for the sensed reduced level of target chemical. The reduction in the amount of treatment fuel additive FA is accomplished by the flow controller 54 sending a signal to the speed/stroke controller 36, which in turn controls a decrease in the speed or stroke of the liquid pump 34 to decrease the flow rate of the fuel additive FA being injected into the fuel within the fuel transport line 12. The decrease in speed/stroke of the liquid pump 34 causes less, or a smaller rate of, fuel additive FA treatment chemical to flow from the fuel additive storage tank 14, through liquid conduit 16, and through additive injection nozzle 46 into the fuel flowing through the fuel transport line 12.

During the fuel processing procedure, the fuel additive processing system 10 is manually monitored in ensure the proper working order of the fuel additive processing system 10. Additionally, the additive chemical level is electronically monitored through the level transmitter 26, the additive chemical temperature is monitored through the temperature sensor/transmitter 22.

The fuel additive flowing through the fuel additive processing system 10 is also monitored at the manual flow indicator 28 prior to the liquid pump 34 and through the pressure gauge 40 subsequent to the liquid pump 34. The flow through the liquid conduit 16 also transmitted from flow transmitter 42.

The system also includes components to ensure the safety and operation of the system. The on/off valve 18 may be closed to prevent the flow of chemical additive from the fuel additive storage tank 14. The safety valve 38 conveys fluid from the liquid conduit 16 back to the fuel additive storage tank 14 should a high threshold pressure within the liquid conduit 16 be reached. Also, the check valve 44 prevents the backflow of fluids from the fuel transport line 12 into the fuel additive processing system 10.

The following is a more detailed example of the fuel additive processing system 10 operation in reference to the treatment of crude oil.

An outgoing volume of crude oil cargo has been found to contain 100 parts per million (ppm) of H2S. This amount of H2S should be reduced below 10 ppm for safe barge loading and transport. The fuel additive FA is a H2S scavenger that consumes H2S at a ratio of two parts H2S to 1 part additive with minimal reaction time and the system's analyzer returns results instantly.

Initially, a desired injection concentration of fuel additive FA may be 50 ppm into the flow controller 54 (specifically the flow control's HMI (human-machine interface), which can be local, remote via cloud, or both). The flow controller 54 is programmed to take user input of concentration and instrument inputs of fuel cargo flow and H2S and calculate an output signal that will control the liquid pump 34 to inject 0-80 GPH such that the crude oil is loaded at tanker B at between 1 ppm to 10 ppm H2S.

The flow rate transmitter 50 transmits the crude oil flow rate through the fuel transport line 12 to the flow controller 54. The flow controller then sends a control signal to the speed/stroke controller 36, adjusting the pump rate proportionally to maintain a 50 ppm injection rate. As the load rate increased to its maximum of 10,000 BBL/HR, the crude oil (fuel) and fuel additive FA rates changes from 0, 5,000 and 10,000 BBL/HR and 0, 10.5 and 21 GPH, respectively.

Simultaneously, the (H2S) chemical or physical property analyzer 52 sends the sensed H2S data from the crude oil stream within the fuel transport line 12 to the flow controller 54. In the event that the cargo exceeds the acceptable limit of 10 ppm, the flow controller 54 recalculates the injection rate with the excess H2S as an addition to the initial input of 50 ppm. If the chemical or physical property analyzer 52 detects 25 ppm of the target chemical H2S while loading at 10,000 BBL/HR, the flow controller 54 initiates the new target ppm as 62.5 and adjust the injection rate to 26.25 GPH through operation of the speed/stroke controller 36 and liquid pump 34. In the event that analyzer 52 detects 0 ppm H2S, an excessive wasteful amount of additive might be injected. In order to prevent this waste, the flow controller has been programmed to gradually decrease additive rate when the analyzer detects 0 ppm. In this example of 10,000 BBL/HR load rate, each 0 ppm result would direct the controller to reduce additive injection rate by 5 ppm, or 2.1

GPH. To obtain useful feedback from the analyzer, the loop must factor in the time required for rate changes made at the injection point to take effect and be observed by the analyzer. Parameters of interest include cargo line displacement between injection point and analyzer, analyzer speed, cargo transfer rate, and additive reaction rate. In this example we assume that the additive reacts instantly and that the displacement between injection point and analyzer is 500 BBLs. At 10,000 BBL/HR transfer rate, the flow controller would recalculate injection rate based on analyzer input every 3 minutes. As the transfer rate changes, the flow controller would recalculate its analysis window proportionally to transfer rate. If the analyzer provides results in the range of 1-10 ppm, no adjustment is made to the additive rate save for injecting proportionally to the cargo transfer rate.

The inputs are continuously monitored by the flow controller 54 to create a 0-100% signal to the stroke controller 36 with this relationship:

$$\frac{\frac{[\text{Manual ppm Input} + \text{Analyzer ppm Input}]}{2}}{1{,}000{,}000} * \text{Cargo Rate}\left(\frac{BBL}{HR}\right)*$$

$$\frac{42\left(\frac{GAL}{BBL}\right)}{80} * 100\% = 80 \text{ } GPH \text{ Injection Pump Stroke Setting}$$

Where the Analyzer PPM Input (API) is determined via a scripted loop duplicating the following instructions:
1. Set API=0
2. If H2S detected is greater than 0 ppm, set Loop Count to 0.
3. If H2S detected is greater than or equal to 10 ppm, API is H2S detected.
4. If H2S detected is 0 ppm, increase Loop Count by 1.
5. If H2S detected is 0 ppm, API is −5*(Loop Count).
6. Set Analysis Window equal to Cargo Transfer Rate (BBL/min)/500 BBL
7. Repeat loop in number of minutes equal to Analysis Window.

With the present fuel additive processing system 10 the additive chemical or fuel additive FA is continuously added into the flowing fuel through fuel transport line 12 in real-time. This provides for a thorough mixing of the additive chemical into the fuel prior to entering the storage tank for a much better treatment of the fuel, as opposed to the prior art batch type processing wherein the additive chemical is added to a vast amount of stagnant fuel in a storage tank after its transportation from one tank to another tank, which may cause an uneven mixing of the additive chemical and fuel resulting in a potentially hazardous untreated amount of fuel to exist within the storage tank. This uneven mixing must be compensated by the adding of a great overabundance of additive chemical or fuel additive FA to ensure thorough treatment of the fuel.

Another significant advantage of the present fuel additive processing system 10 is that by continuously analyzing and determining of the target chemical and the adding of the additive chemical to the flowing fuel in real-time the overabundance of additive chemical is reduced from approximately 40% associated with batch type processing to only 10 to 15%. This real-time processing greatly reduces the requirement for the additive chemical and the costs associated with such. It should be understood that as used herein, the term "continuously" is intended to mean that the analyzing, determining, and adding (injecting) is done throughout the transportation process of the fuel from one storage tank to another storage tank, and that the term "continuously" does not mean that such actions are being done without interruption, as the term also includes a short periodic analyzing, determining or adding, for example, every 5 minutes.

It should be understood that a set increase in the additive flow rate may be calculated for a select chemical additive. For example, the increase or decrease in the additive flow rate may be determined to incremental increase or decrease the volume of fuel additive by 5 ppm. This amount may vary depending on the select fuel additive and select fuel being treated.

Accordingly, it is seen that a need remains for a fuel additive processing system that processes additive chemicals into the fuel in an efficient manner. It is to the provision of such therefore that the present invention is primarily directed.

The invention claimed is:

1. A real-time fuel additive processing system for use in conjunction with a fuel transport line transporting a fuel containing a target chemical or physical property to be treated, the fuel additive processing system comprising:
 a fuel additive storage tank;
 a fuel additive injection nozzle in fluid communication with the fuel transport line;
 a fuel additive liquid conduit extending from said fuel additive storage tank to said fuel additive injection nozzle;
 a liquid pump coupled to said fuel additive liquid conduit;
 a flow rate transmitter for sensing the flow rate of fuel through the fuel transport line and transmitting the sensed flow rate;
 a chemical or physical property analyzer coupled to the fuel transport line for sensing the quantity of a target chemical or physical property within the fuel flowing through the fuel transport line, and
 a flow rate controller electronically coupled to said flow rate transmitter, said chemical or physical property analyzer, and said liquid pump, said flow rate transmitter sending an electronic signal to said flow rate controller indicating the flow rate of liquid through the fuel transport line, said chemical or physical property analyzer sending an electronic signal to said flow rate controller indicating the quantity of a sensed target chemical or physical property within the fuel flowing through the fuel transport line, and the flow rate controller controlling the operation of said liquid pump to control the amount of fuel additive passing through said nozzle and into the fuel flowing through the fuel transport line for the treatment of the target chemical or physical property within the fuel.

2. The fuel additive processing system of claim 1 further comprising a fuel additive for treating the target chemical or physical property.

3. The fuel additive processing system of claim 1 further comprising a flow transmitter coupled to said fuel additive liquid conduit.

4. The fuel additive processing system of claim 1 wherein said chemical or physical property analyzer is a hydrogen sulfide analyzer for sensing a target chemical or physical property of hydrogen sulfide within the fuel flowing through the fuel transport line.

5. The fuel additive processing system of claim 1 wherein said chemical or physical property analyzer is coupled to the transport line downstream of said nozzle with respect to the flow of fuel flowing through the fuel transport line.

6. The fuel additive processing system of claim 1 wherein said flow rate transmitter is coupled to the transport line downstream of said nozzle with respect to the flow of fuel lowing through the fuel transport line.

7. The fuel additive processing system of claim 1 wherein said chemical or physical property analyzer and said flow rate transmitter are coupled to the transport line downstream of said nozzle with respect to the flow of fuel lowing through the fuel transport line.

8. The fuel additive processing system of claim 1 wherein said liquid pump is coupled to said flow controller through a pump speed controller.

9. The fuel additive processing system of claim 1 wherein said flow rate controller controls the speed of said liquid pump to control the amount of fuel additive passing through said nozzle and into the fuel flowing through the fuel transport line for the treatment of the target chemical or physical property within the fuel.

10. A method of processing fuel in real-time comprising the steps of:
  (A) passing a fuel containing a target chemical or physical property to be treated through a fuel transport line;
  (B) continuously determining the flow rate of the fuel passing through the fuel transport line;
  (C) continuously analyzing the fuel passing through the fuel transport line to determine the amount of a target chemical or physical property within the fuel;
  (D) continuously determining the quantity of fuel additive to be injected into the fuel passing through the fuel transport line based upon the flow rate of the fuel in step (B) and the determined amount of target chemical or physical property in the fuel in step (C), and
  (E) continuously injecting a quantity of fuel additive into the fuel passing through the fuel transport line determined in step (D).

11. The method of claim 10 wherein the target chemical or physical property is hydrogen sulfide and the fuel additive is a hydrogen sulfide scavenging chemical.

12. The method of claim 10 wherein step (B) the flow rate is determined from the fuel passing through the fuel transport line is conducted downstream of the injecting of the fuel additive into the fuel passing through the fuel transport line.

13. The method of claim 10 wherein step (C) the analyzing of the fuel is determined from the fuel passing through the fuel transport line is conducted downstream of the injecting of the fuel additive into the fuel passing through the fuel transport line.

14. A method of processing flowing fuel passing through a fuel transport line comprising the steps of:
  (A) providing a fuel additive storage tank containing a volume of fuel additive, a fuel additive injection nozzle in fluid communication with the fuel transport line, a fuel additive liquid conduit extending from the fuel additive storage tank to the fuel additive injection nozzle, a liquid pump coupled to the fuel additive liquid conduit, a flow rate transmitter for sensing the flow rate of fuel through the fuel transport line and transmitting the sensed flow rate, a chemical or physical property analyzer coupled to the fuel transport line for sensing the quantity of a target chemical or physical property within the fuel flowing through the fuel transport line, and a flow rate controller electronically coupled to the flow rate transmitter, the chemical or physical property analyzer, and the liquid pump
  (B) sensing the flow rate of the fuel passing through the fuel transport line and sending a signal of the sensed flow rate from the flow rate transmitter to the flow rate controller;
  (C) sensing the quantity of target chemical or physical property within the fuel passing through the fuel transport line through the chemical or physical property analyzer and sending an electronic signal of the sensed quantity of target chemical or physical property to the flow rate controller;
  (D) determining a quantity of fuel additive to be added to the fuel flowing through the fuel transport line by the flow rate controller, and
  (E) sending an electronic signal from the flow rate controller to the liquid pump to control the operation of the liquid pump to regulate the amount of fuel additive passing through the nozzle and into the fuel flowing through the fuel transport line for the treatment of the target chemical or physical property within the fuel.

15. The method of claim 14 wherein the target chemical or physical property is hydrogen sulfide and the fuel additive is a hydrogen sulfide scavenging chemical.

16. The method of claim 14 wherein the target chemical or physical property is hydrogen sulfide and the fuel additive is a hydrogen sulfide scavenging chemical.

17. The method of claim 14 wherein step (B) the flow rate is determined from the fuel passing through the fuel transport line is conducted downstream of the nozzle in step (E).

18. The method of claim 14 wherein step (C) the analyzing of the fuel is determined from the fuel passing through the fuel transport line is conducted downstream of the nozzle in step (E).

* * * * *